United States Patent [19]
Ichikawa et al.

[11] Patent Number: 5,272,126
[45] Date of Patent: Dec. 21, 1993

[54] ADSORPTION TYPE PACKING FOR GAS CHROMATOGRAPHY AND PROCESS FOR PRODUCING THE SAME

[75] Inventors: Hiroshi Ichikawa; Akira Yokoyama; Keiichi Hirata, all of Yokohama, Japan; Hiroo Wada; Kenzo Kotera, both of Kyatu Shi, all of Japan

[73] Assignees: Nippon Carbon Co., Ltd., Tokyo; Shinwa Chemical Industries, Ltd., KuKyoto, both of Japan

[21] Appl. No.: 865,305

[22] Filed: Apr. 8, 1992

[51] Int. Cl.$^5$ .............. C01B 31/14; B01J 20/20; B01J 20/28; G01N 30/48
[52] U.S. Cl. .............. 502/429; 264/29.5; 502/416; 502/428; 502/432; 502/437; 95/88
[58] Field of Search .............. 502/429, 428, 432, 437; 264/29.5, 29.3

[56] References Cited

U.S. PATENT DOCUMENTS

| | | | |
|---|---|---|---|
| 4,124,529 | 11/1978 | Jungtem et al. | 264/29.1 |
| 4,933,314 | 6/1990 | Marumio et al. | 502/432 |
| 4,978,650 | 12/1990 | Coughlin et al. | 55/74 |
| 5,071,450 | 12/1991 | Cabrera | 502/437 |
| 5,071,820 | 12/1991 | Quinn et al. | 502/437 |
| 5,094,754 | 3/1992 | Maroldo et al. | 210/635 |
| 5,098,880 | 3/1992 | Gaffney et al. | 502/437 |
| 5,118,329 | 6/1992 | Kosaka et al. | 55/74 |
| 5,164,355 | 11/1992 | Farris et al. | 55/74 |

FOREIGN PATENT DOCUMENTS

| | | |
|---|---|---|
| 0198171 | 10/1986 | European Pat. Off. |
| 439247 | 7/1991 | European Pat. Off. |
| 2946668 | 6/1980 | Fed. Rep. of Germany |

OTHER PUBLICATIONS

Database WPIL, Week 9230, Derwent Publications Ltd., Londi, GB; LAN 92-246501 & JP-A-4 166 763 (Nippon Carbon Co. Ltd.) Jun. 12, 1992.

*Primary Examiner*—Paul E. Konopka
*Attorney, Agent, or Firm*—Bucknam and Archer

[57] ABSTRACT

An adsorption type packing for gas chromatography composed of finely divided carbon particles in whole, and having a ratio of nitrogen gas adsorption at a relative pressure of 0.3 ($V_{0.3}$) to nitrogen gas adsorption at a relative pressure of about 1.0 ($V_{1.0}$) each in the adsorption isotherm of said packing, $V_{0.3}/V_{1.0}$, of 0.9 or more and a BET specific surface area of 1,000 to 2,000 m$^2$/g; and a process for producing said packing.

10 Claims, 3 Drawing Sheets

RETENTION TIME

ADSORPTION TYPE PACKING FOR GAS CHROMATOGRAPHY AND PROCESS FOR PRODUCING THE SAME

BACKGROUND OF THE INVENTION

1. Field of the Invention

The present invention relates to adsorption type packings for gas chromatography capable of simultaneously analyzing five kinds of gases including $O_2$, $N_2$, $CH_4$, CO and $CO_2$ and usable over a wide range, and to a process for producing the packings.

2. Prior Art

With regard to gas analysis in which gas chromatography is utilized, adsorption type packings, such as molecular sieve, silica gel or granular activated carbon, have heretofore been employed.

These packings, however, suffer such a disadvantage that they are incapable of simultaneously analyzing five kinds of gases including $O_2$, $N_2$, $CH_4$, CO and $CO_2$, each being the most important gas in gas analysis. Specifically, $CO_2$ is not eluted from molecular sieve, and separation of $O_2$ from $N_2$ is impossible with silica gel or activated carbon.

Accordingly, there has heretofore been used a method wherein two columns, one packed with molecular sieve and the other with porous polymer beads, are connected in parallel to use the former for analyzing $O_2$, $N_2$, $CH_4$, and CO, while the latter for $CO_2$.

Since in the above-mentioned method, the flow rate control of the gas to be fed to each of the two columns is extremely difficult, it has long been desired to develop a packing capable of simultaneously analyzing the five kinds of gases by the use of a single column.

SUMMARY OF THE INVENTION

It is an object of the present invention to overcome the foregoing disadvantage and provide an adsorption type packing for gas chromatography capable of simultaneously analyzing five kinds of gases including $O_2$, $N_2$, $CH_4$, CO and $CO_2$ and usable over a wide range.

It has been found by the present inventors that the inseparability of $O_2$ from $N_2$ with the conventional granular activated carbon is caused by the fact that the coexistence of micropores and macropores in the activated carbon makes the desorption of the adsorbed matters difficult, and by the limited number of micropores participating in the separation of $O_2$ from $N_2$ due to the small surface area of the raw material for the activated carbon.

In view of the above, intensive studies have been made by the present inventors on a packing having a large number of micropores participating in the separation of $O_2$ from $N_2$ and not including macropores and on a process for producing the packing.

As the result of the studies, the present inventors have found that the use of finely divided carbon particles as the raw material serves to increase the surface area of the aggregates and produce a packing having numerous micropores almost free from macropores by activating the aggregates and that the separability of $O_2$ from $N_2$ is improved and the simultaneous analysis of $O_2$, $N_2$, $CH_4$, CO and $CO_2$ is maybe carried out by adjusting the ratio of nitrogen gas adsorption at a relative pressure of 0.3 ($V_{0.3}$) to nitrogen gas adsorption at a relative pressure of about 1.0 ($V_{1.0}$) each in the adsorption isotherm of the above packing, $V_{0.3}/V_{1.0}$, to 0.9 or more and, at the same time, the BET specific surface area of the packing to 1,000 to 2,000 $m^2/g$.

The present invention has been accomplished on the basis of this finding.

Specifically, the present invention relates to a packing for gas chromatography comprising activated carbon having micropores free from macropores and a specific surface area of 1,000 to 2,000 $m^2/g$, said activated carbon being produced by activating aggregates of finely divided carbon particles having a large surface area.

The adsorption type packing for gas chromatography of the present invention is composed of finely divided carbon particles entirely, and has a ratio of nitrogen gas adsorption at a relative pressure of 0.3 ($V_{0.3}$) to nitrogen gas adsorption at a relative pressure of about 1.0 ($V_{1.0}$) each in the adsorption isotherm of said packing, $V_{0.3}/V_{1.0}$, of 0.9 or more and a BET specific surface area of 1,000 to 2,000 $m^2/g$.

Further, the process of the present invention for producing the packing comprises the steps of uniformly applying a thermosetting resin as the coating material to a nonfusible and carbonizable high-molecular compound in finely divided form or a carbonized product thereof, or a high-molecular compound in finely divided form which can be made nonfusible and carbonizable by various treatments or a carbonized product thereof; forming the coated product; subjecting the formed product to curing, firing, dividing and classifying to obtain aggregates of finely divided carbon particles having a uniform particle size; activating the aggregates; and acid-treating the activated aggregates.

By the term "nonfusible and carbonizable high-molecular compound in finely divided form or carbonized product thereof" as used herein is meant a compound which can be carbonized without being fused during the heat treatment causing carbonization. The use of such a compound enables the shape retention of the finely divided particles as the raw material and the production of the aggregates of the finely divided carbon particles.

The nonfusible and carbonizable high-molecular compounds in finely divided form include thermosetting resins such as nonfusible phenolic resin, rayon and PAN. The compounds which can be made nonfusible and carbonizable by various treatments include pitch and lignin.

The thermosetting resin solutions used as the coating material include those of phenol, modified phenol and furan resins.

Preferably, 5 to 100 parts by weight of the thermosetting resin is compounded with 100 parts by weight of the finely divided particles of the high-molecular compound or carbonized product thereof. The thermosetting resin in a loading of less than 5 parts by weight causes a decrease in the packing strength leading to easy pulverization of the packing, whereas that of more than 100 parts by weight causes a decrease in the surface area of the aggregates of the finely divided carbon particles, thereby making it impossible to produce a packing having micropores free from macropores and a specific surface area of 1,000 to 2,000 $m^2/g$.

The content of the finely divided particles having a particle diameter of 100 $\mu$m or smaller should be 90% or more by weight, since the content of those having a particle diameter exceeding 100 $\mu$m of 10% or more by weight makes it impossible to produce a packing having micropores free from macropores and a specific surface area of 1,000 to 2,000 m²/g.

When the finely divided particles are coated with a thermosetting resin, a solvent is used for the resin so as to uniform the coating. The usable solvents include alcohols, such as methanol and ethanol, and ketones such as acetone and methyl ethyl ketone.

The compounding ratio of the solvent to the thermosetting resin should be at least 1/1. The compounding ratio less than 1/1 makes it impossible to uniformly apply the thermosetting resin to the finely divided particles, thus decreasing the strength of the packing as the final product.

Subsequently, by drying the slurried thermosetting resin to remove the solvent used, the finely divided particles are uniformly coated with the resin.

In this case, the coating is preferably effected under reduced pressure in the temperature range not causing the resin to be cured, for example, at 80° C. or lower.

Subsequently, the coated finely divided particles are formed.

Methods of the forming include a method in which the coated finely divided particles are extruded from a nozzle of 150 to 500 μm in pore diameter to form into a bar, a method of molding with a mold, etc., and extrusion forming is particularly desirable from the viewpoint of the characteristics and pulverizability of the forming obtained.

The reason of effecting forming prior to heat treatment is that heat treatment as such prior to forming makes the aggregates thus obtained nonuniform.

Subsequently, the formed product is cured by heating at 100° to 200° C. for 1 to 5 hours, further fired in an inert gas atmosphere at 600° to 1,000° C., divided and classified to give granular aggregates of 60- to 80-mesh and 80- to 100- mesh finely divided carbon particles.

In activating the aggregates of the finely divided carbon particles thus obtained, the ratio of nitrogen gas absorption at a relative pressure of 0.3 ($V_{0.3}$) to nitrogen adsorption at a relative pressure of about 1.0 ($V_{1.0}$) each in the adsorption isotherm, $V_{0.3}/V_{1.0}$, can be adjusted to 0.9 or more and, at the same time, the BET specific surface area can be adjusted to 1,000 to 2,000 m²/g by suitably adjusting the activation temperature, activation time and the amount of steam to be used.

The above-mentioned object can be attained by activating the aggregates at 900° to 1,000° C. for 10 to 60 minutes at a steam flow rate of 1 to 10 cc/minute.

The $V_{0.3}/V_{1.0}$ ratio or the specific surface area less than the foregoing value or outside the range, respectively makes it impossible to favorably separate $O_2$ from $N_2$.

The activation methods include the activation with carbon dioxide, and that with a chemical in addition to the activation with steam, which however, is most preferable.

As the last step, the above activated aggregates of the finely divided carbon particles are subjected to acid treatment to neutralize the alkali formed during the activation, thus making $CO_2$ analysis possible. The acid to be used in the acid treatment is preferably hydrochloric acid as a volatile acid.

The packing thus obtained is capable of simultaneously analyzing five kinds of gases including $O_2$, $N_2$, $CH_4$, CO and $CO_2$ and is usable over a wide range of analysis.

Effect of the Invention

The adsorption type packing for gas chromatography according to the present invention is capable of simultaneously analyzing five kinds of gases including $O_2$, $N_2$, CO, $CH_4$ and $CO_2$ and is usable over a wide range of analysis.

PREFERRED EMBODIMENTS OF THE INVENTION

The present invention will be described in more detail with reference to the following Examples and Comparative Examples, though it should be understood that the present invention is not limited thereto.

EXAMPLE 1

Five hundreds (500) g of a nonfusible phenol resin (trade name: Univeks C-30, produced by Unitika Ltd., Japan) having a particle diameter of 10 to 30 μm was mixed with 150 g of a phenol resin solution (trade name: TD-753S, produced by Dainippon Ink and Chemicals, Inc., Japan) and 150 g of methanol to form a slurry, which was then dried at 50° C. under reduced pressure to remove the methanol. The resultant dried product was extruded from a nozzle with a pore diameter of 300 μm for forming, and cured by heating at 150° C. for 1 hour, followed by firing at 700° C. The fired product was divided and classified to afford the aggregates of the finely divided carbon particles uniformed to 60 to 80 mesh in terms of particle size.

The aggregates of the finely divided carbon particles were activated at 950° C. for 60 minutes in a steam atmosphere, treated with 6N-HCl, and dried to give an adsorption type packing for gas chromatography.

Figure 1:
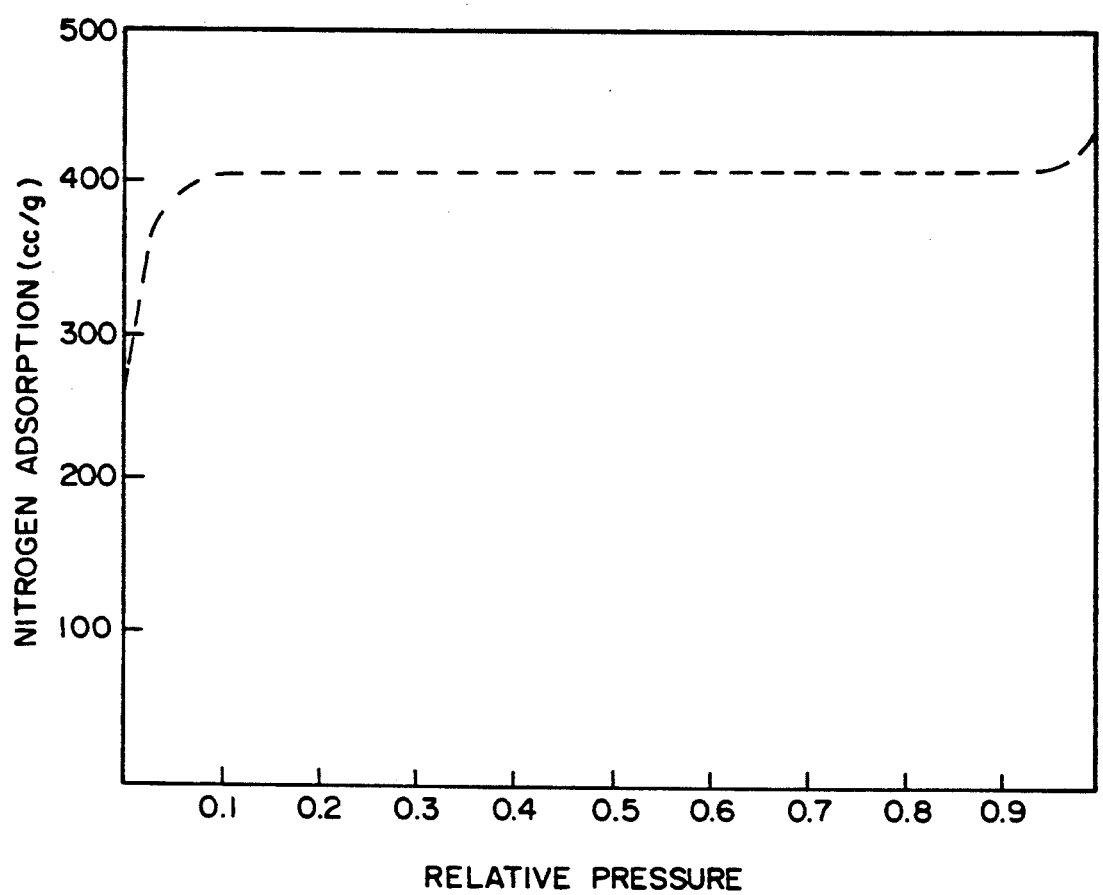
FIG. 1 shows the adsorption isotherm of a packing of the present invention.

The packing thus obtained had a specific surface area of 1,500 m²/g and a $V_{0.3}/V_{1.0}$ ratio obtained from the adsorption isotherm in FIG. 1 of 0.99 and was almost free from macropores.

Figure 2:
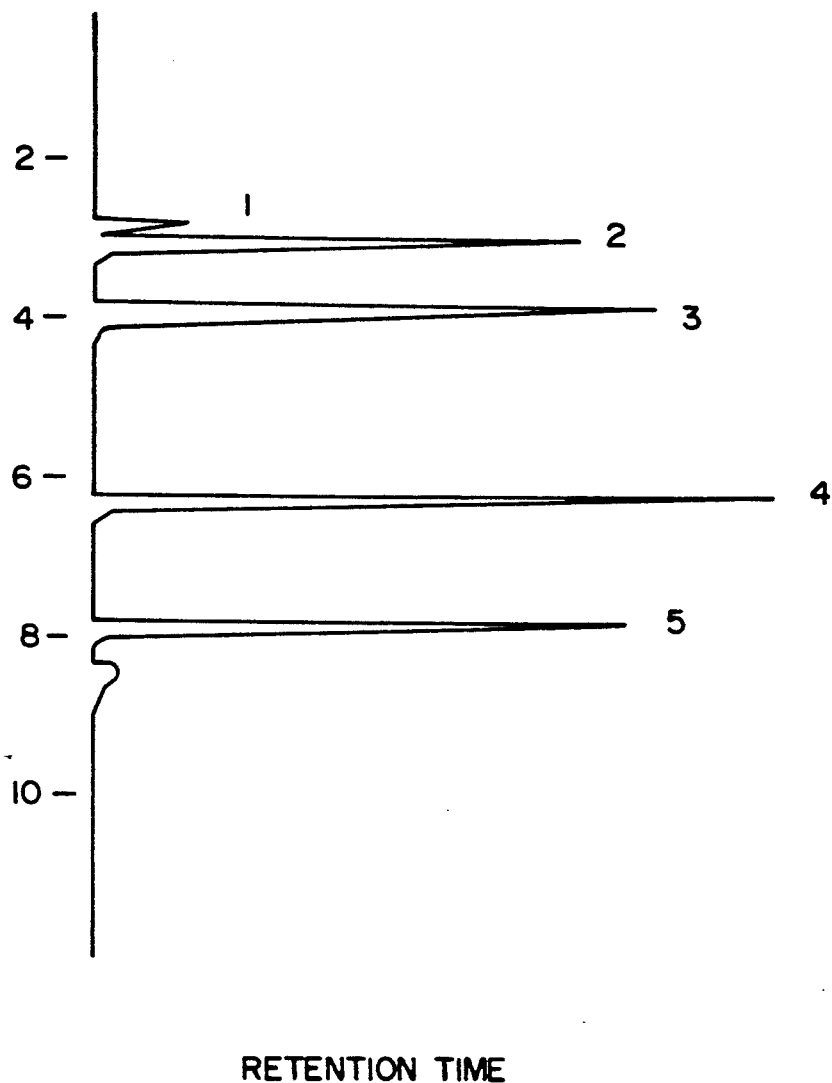
FIG. 2 shows an example of gas chromatogram for the analysis of several compounds by the use of the packing according to the present invention.

Subsequently, the packing was packed in a column of 3.2 mm in diameter and 3.0 m in length to be used for analyzing $O_2$, $N_2$, CO, $CH_4$ and $CO_2$ by gas chromatography. As can be seen in FIG. 2, the result of the analysis demonstrated favorable separation of the gases from one another.

COMPARATIVE EXAMPLE 1

A commercially available granular activated carbon (trade name: JXN, produced by Nippon Carbon Co., Ltd., Japan) was divided, classified and uniformed to 60 to 80 mesh and subsequently treated with hydrochloric acid in the same manner as the one in Example 1 to give an adsorption type packing for gas chromatography.

Figure 3:
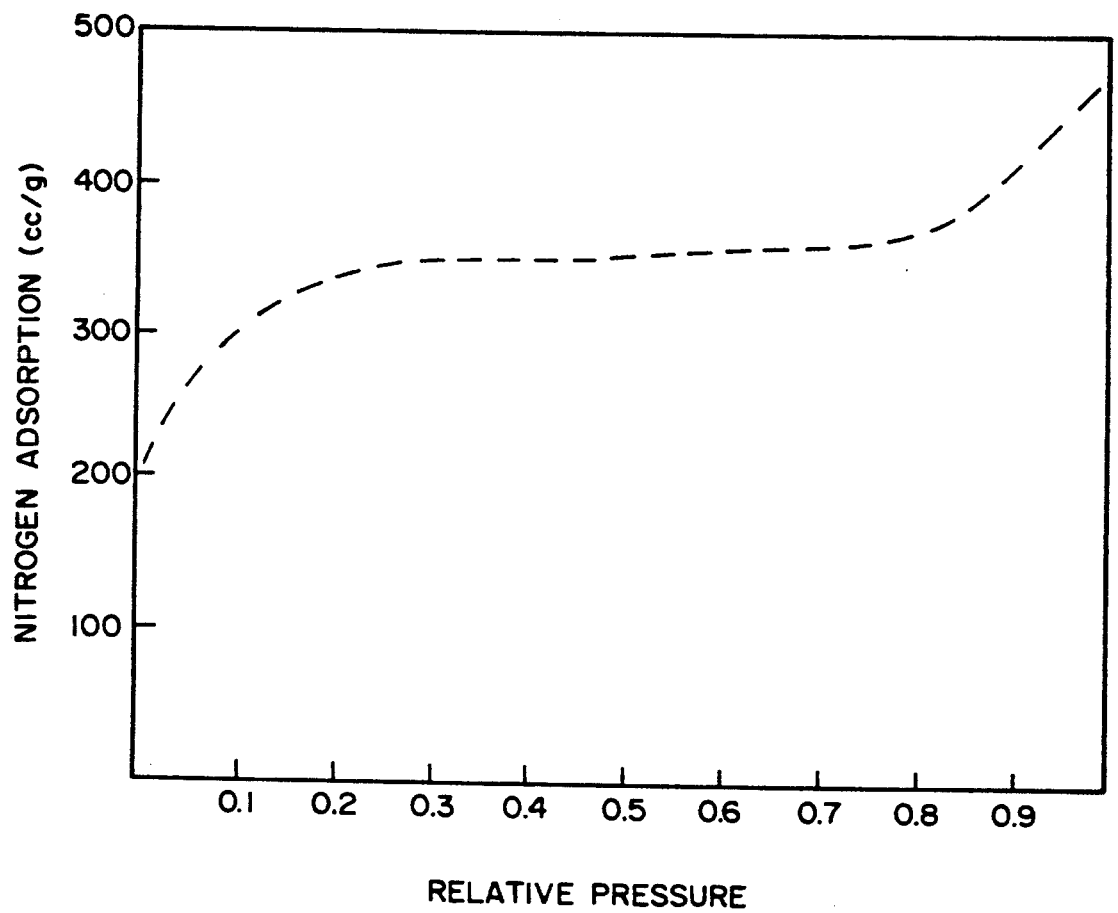
FIG. 3 shows an adsorption isotherm of an adsorption type packing for gas chromatography obtained from a commercially available granular activated carbon.

The packing thus obtained had a specific surface area of 1,200 m²/g and a $V_{0.3}/V_{1.0}$ ratio obtained from the adsorption isotherm in FIG. 3 of 0.70, which proved the coexistence of both micropores and macropores.

Subsequently, the packing was packed in a column of 3.2 mm in diameter and 3 m in length to be used for analyzing air by gas chromatography under the conditions same as those in the Example 1. As a result, no separation of $O_2$ from $N_2$ was observed at all.

COMPARATIVE EXAMPLE 2

The aggregates of the finely divided carbon particles obtained in Example 1 were activated at 850° C. for 60 minutes in a steam atmosphere, treated with 6N-HCl and dried to give a packing having a specific surface area of 700 $m^2/g$ and a $V_{0.3}/V_{1.0}$ ratio obtained from the adsorption isotherm of 0.95. The packing thus obtained was used for analyzing air by gas chromatography under the conditions same as those in Example 1. As a result, no separation of $O_2$ from $N_2$ was observed at all.

What is claimed is:

1. A process for producing an adsorption packing for gas chromatography consisting of finely divided carbon particles and having a ratio of nitrogen gas adsorption at a relative pressure of 0.3 ($V_{0.3}$) to nitrogen gas adsorption at a relative pressure of about 1.0 ($V_{1.0}$) each in the adsorption isotherm of said packing, $V_{0.3}/V_{1.0'}$ of 0.9 or more and a BET specific surface area of 1,000 to 2,000 $m^2/g$, which consists essentially of the steps of
   a) preparing a slurry of
      (i) finely divided particles of a nonfusible and carbonizable thermosetting resin or carbonized particles thereof, at least 90% by weight having a particle diameter of 100 $\mu m$ or less,
      (ii) a thermosetting resin solution in an amount of 5 to 100 parts by weight based on 100 parts by weight of said particles (i), and
      (iii) a solvent in a mixing ratio of said solvent (iii) to said thermosetting resin solution (ii) of at least 1/1;
   b) drying said slurry to remove the solvent (iii) whereby said finely divided particles (i) uniformly coated with said thermosetting resin (ii) are obtained;
   c) forming the coated particles from step b) to obtain a shaped product;
   d) curing said shaped product from step c) by heating at a temperature in the range of 100° to 200° C. for 1 to 5 hours to obtain a cured product;
   e) firing said cured product from step a) in an inert gas atmosphere at a temperature in the range of 600° to 1,000° C. to obtain a fired product;
   f) dividing and then classifying said fired product to obtain granular aggregates of finely divided carbon particles having a uniform particle size of 60- to 100-mesh;
   g) activating said aggregates from step f) at a temperature in the range of 900° to 1,000° C. for 10 to 60 minutes at a steam flow rate of 1 to 10 cc/min. to obtain activated aggregates; and
   h) treating said activated aggregates from step g) with an acid to neutralize the alkali formed during the activation in step g).

2. The process according to claim 1, wherein said nonfusible and carbonizable thermosetting resin (i) is a member selected from the group consisting of nonfusible phenolic resin, rayon and PAN.

3. The process according to claim 1, wherein said thermosetting resin solution (ii) is a member selected from the group consisting of phenol-, modified phenol- and furan-resin solutions.

4. The process according to claim 1, wherein said solvent (iii) is a member selected from the group consisting of methanol, ethanol, acetone and methyl ethyl ketone.

5. The process according to claim 1, wherein said slurry is dried in step (b) under a reduced pressure at a temperature of 80° C. or less.

6. The process according to claim 1, wherein said coated particles in step (c) are extruded from a nozzle of 150 to 500 $\mu m$ in pore diameter to form a bar-shaped product.

7. The process according to claim 1, wherein said acid is hydrochloric acid in step (h).

8. The process according to claim 1, wherein said adsorption packing is capable of simultaneously analyzing five gases including $O_2$, $N_2$, $CH_4$, CO and $CO_2$.

9. The process according to claim 8, wherein said packing is essentially free of macropores.

10. The process according to claim 2, wherein in step (a), said slurry is prepared from 5-100 parts of said thermosetting resin and 100 parts of said finely divided particles (i).

* * * * *